(12) United States Patent
Luo et al.

(10) Patent No.: US 10,898,669 B2
(45) Date of Patent: Jan. 26, 2021

(54) CARBON DIOXIDE INHALATION TREATMENT DEVICE FOR CENTRAL SLEEP APNEA

(71) Applicant: Yuanming Luo, Guangzhou (CN)

(72) Inventors: Yuanming Luo, Guangzhou (CN); Zhihui Qiu, Guangzhou (CN); Yingmei Luo, Guangzhou (CN); Yongyi Chen, Guangzhou (CN); Michael Iain Polkey, London (GB)

(73) Assignee: Yuanming Luo, Guangzhou (CN)

( * ) Notice: Subject to any disclaimer, the term of this patent is extended or adjusted under 35 U.S.C. 154(b) by 878 days.

(21) Appl. No.: 15/494,137

(22) Filed: Apr. 21, 2017

(65) Prior Publication Data

US 2017/0333664 A1  Nov. 23, 2017

(30) Foreign Application Priority Data

Apr. 21, 2016 (CN) .......................... 2016 1 0251692

(51) Int. Cl.
*A61M 16/12* (2006.01)
*A61B 5/0476* (2006.01)
(Continued)

(52) U.S. Cl.
CPC ....... *A61M 16/125* (2014.02); *A61B 5/04012* (2013.01); *A61B 5/0476* (2013.01);
(Continued)

(58) Field of Classification Search
CPC .......... A61M 16/0066; A61M 16/0069; A61M 16/0045; A61M 16/12; A61M 16/122;
(Continued)

(56) References Cited

U.S. PATENT DOCUMENTS 2,843,121 A * 7/1958 Hudson ................. A61M 16/06
128/206.24
3,974,830 A * 8/1976 LaVerne ........... A61M 16/0045
128/203.27
(Continued)

FOREIGN PATENT DOCUMENTS

CN  200720172764  7/2008
CN  200780018415  6/2009
(Continued)

*Primary Examiner* — Kathryn E Ditmer
(74) *Attorney, Agent, or Firm* — JMB Davis Ben-David

(57) ABSTRACT

The present invention discloses a carbon dioxide inhalation treatment device for central sleep apnea comprising a blower, a gas cylinder filled with carbon dioxide ($CO_2$), an airbag, a mask, and a detection mechanism for detecting the central apnea by measuring the electromyographic activity of the chest wall muscles. The mask is provided with multiple holes providing a communication between the inside and outside of the mask in order to prevent any sense of resistance of breathing and to provide greater control of inspired $CO_2$. Inspired $CO_2$ from a gas mixture containing also a minimum 20% $O_2$ is driven by air using a blower into a mixing chamber. This carbon dioxide inhalation treatment device for central sleep apnea can provide a stable, mild level of carbon dioxide for patients with central sleep apnea, thus by preserving respiratory drive correcting central sleep apnea without increasing the arousal and microarousal frequency.

11 Claims, 2 Drawing Sheets

(51) Int. Cl.
| | |
|---|---|
| *A61M 16/00* | (2006.01) |
| *A61B 5/0488* | (2006.01) |
| *A61B 5/04* | (2006.01) |
| *A61B 5/0478* | (2006.01) |
| *A61B 5/0492* | (2006.01) |
| *A61B 5/00* | (2006.01) |
| *A61M 16/06* | (2006.01) |
| *A61M 16/10* | (2006.01) |

(52) U.S. Cl.
CPC .......... *A61B 5/0478* (2013.01); *A61B 5/0488* (2013.01); *A61B 5/0492* (2013.01); *A61B 5/4818* (2013.01); *A61B 5/4839* (2013.01); *A61B 5/746* (2013.01); *A61M 16/0045* (2013.01); *A61M 16/0051* (2013.01); *A61M 16/0069* (2014.02); *A61M 16/06* (2013.01); *A61M 16/0683* (2013.01); *A61M 2016/103* (2013.01); *A61M 2202/0208* (2013.01); *A61M 2202/0225* (2013.01); *A61M 2210/1014* (2013.01); *A61M 2230/10* (2013.01); *A61M 2230/60* (2013.01)

(58) Field of Classification Search
CPC ........ A61M 16/125; A61M 2202/0225; A61M 5/0476; A61M 5/0478; A61M 5/0488; A61M 5/0492; A61M 5/4818; A61M 5/4839; A61M 4/746
See application file for complete search history.

(56) References Cited

U.S. PATENT DOCUMENTS

| | | | | |
|---|---|---|---|---|
| D250,131 S * | 10/1978 | Lewis | | 128/206.28 |
| 4,201,205 A * | 5/1980 | Bartholomew | | A61M 16/06 128/205.25 |
| 4,328,797 A * | 5/1982 | Rollins, III | | A61M 16/06 128/202.15 |
| 4,554,916 A * | 11/1985 | Watt | | A61M 16/12 128/200.19 |
| 5,400,781 A * | 3/1995 | Davenport | | A61M 16/06 128/206.28 |
| 5,540,233 A * | 7/1996 | Larsson | | A61B 5/0813 600/532 |
| 5,887,611 A * | 3/1999 | Lampotang | | A61M 16/12 137/101.19 |
| 5,924,419 A * | 7/1999 | Kotliar | | A23L 3/3418 128/200.24 |
| 6,752,150 B1 * | 6/2004 | Remmers | | A61M 16/0009 128/204.18 |
| 7,040,319 B1 * | 5/2006 | Kelly | | A61M 16/06 128/204.22 |
| 7,150,717 B2 * | 12/2006 | Katura | | A61B 5/02055 600/504 |
| 7,516,742 B2 * | 4/2009 | Stenzler | | A61M 16/203 128/204.23 |
| 8,545,416 B1 * | 10/2013 | Kayyali | | A61B 5/085 600/534 |
| 10,226,591 B1 * | 3/2019 | Tarler | | A61M 16/022 |
| 10,231,864 B1 * | 3/2019 | Webster | | A61M 16/0666 |
| 2002/0112722 A1 * | 8/2002 | Carter | | A61M 16/12 128/203.12 |
| 2002/0112726 A1 * | 8/2002 | Schmidt | | A61M 16/0677 128/204.23 |
| 2002/0185129 A1 * | 12/2002 | Fisher | | A61B 5/4821 128/203.25 |
| 2004/0144383 A1 * | 7/2004 | Thomas | | A61M 16/12 128/204.18 |
| 2004/0255939 A1 * | 12/2004 | Feldman | | A61M 16/12 128/203.12 |
| 2005/0085868 A1 * | 4/2005 | Tehrani | | A61N 1/3601 607/42 |
| 2005/0113709 A1 * | 5/2005 | Millet | | A61B 5/08 600/529 |
| 2005/0115561 A1 * | 6/2005 | Stahmann | | A61B 5/4818 128/200.24 |
| 2006/0195041 A1 * | 8/2006 | Lynn | | A61B 5/412 600/538 |
| 2008/0302364 A1 * | 12/2008 | Garde | | A61M 16/201 128/204.23 |
| 2009/0120435 A1 * | 5/2009 | Slessarev | | A61M 16/08 128/203.14 |
| 2010/0139659 A1 * | 6/2010 | von Blumenthal | | A61M 16/12 128/204.23 |
| 2010/0224191 A1 * | 9/2010 | Dixon | | A61B 5/14539 128/204.23 |
| 2011/0290252 A1 * | 12/2011 | Amjad | | A61M 16/026 128/204.23 |
| 2012/0006326 A1 * | 1/2012 | Ahmad | | A61M 16/024 128/204.22 |
| 2013/0109978 A1 * | 5/2013 | Fisher | | A61B 5/7278 600/484 |
| 2013/0239968 A1 * | 9/2013 | Friberg | | A61M 16/01 128/204.23 |
| 2014/0051938 A1 * | 2/2014 | Goldstein | | A61B 5/4818 600/301 |
| 2014/0123980 A1 * | 5/2014 | Rissacher | | A61M 16/0683 128/204.23 |
| 2014/0158124 A1 * | 6/2014 | L'her | | A61M 16/203 128/203.14 |
| 2014/0216455 A1 * | 8/2014 | Kelly | | A61M 16/0069 128/203.12 |
| 2015/0151073 A1 * | 6/2015 | Shushunov | | A61M 16/0045 128/203.26 |
| 2015/0217075 A1 * | 8/2015 | Nair | | A61B 1/01 600/531 |
| 2015/0328417 A1 * | 11/2015 | Loser | | A61M 16/024 128/204.23 |
| 2016/0082220 A1 * | 3/2016 | Barker | | A61M 16/1005 128/203.12 |
| 2016/0287824 A1 * | 10/2016 | Chang | | A61M 16/0051 |
| 2017/0232214 A1 * | 8/2017 | Walsh | | A61M 16/021 128/202.22 |

FOREIGN PATENT DOCUMENTS

| | | |
|---|---|---|
| CN | 200680056910 | 2/2010 |
| CN | 201320673950 | 6/2014 |
| CN | 201280051395 | 7/2014 |
| CN | 20162034094 | 11/2016 |

\* cited by examiner

CARBON DIOXIDE INHALATION TREATMENT DEVICE FOR CENTRAL SLEEP APNEA

FIELD OF THE INVENTION

The present invention relates to a treatment device, and in particular to a carbon dioxide inhalation treatment device for central sleep apnea.

BACKGROUND OF THE INVENTION

Carbon dioxide is a respiratory center stimulant. Normal breathing rhythm depends on a constant level of carbon dioxide maintained in the body. Within a certain range, if the concentration of carbon dioxide in the blood is too high, carbon dioxide will stimulate the brain stem chemoreceptor to make breathing deepened and accelerated; conversely apnea will be caused when the concentration of carbon dioxide in the blood is reduced. In the awake state, respiratory depression due to a decrease in the concentration of carbon dioxide in the blood can be compensated by excitability in the cerebral cortex, thereby maintaining the normal breathing motion. However, in the asleep state, a decrease in the concentration of carbon dioxide in the blood can cause sleep apnea.

Heart failure patients often suffer from frequent episodes of central sleep apnea which results in intermittent hypoxia and this is considered harmful since it may further damage heart function and is associated with increased mortality in the patients with heart failure. Inhaled carbon dioxide can eliminate central sleep apnea and Improve heart function. However, inhalation of excessive carbon dioxide can cause arousal, affect sleep and aggravate the condition; equally if concentration of the inhaled carbon dioxide is too low, the central sleep apnea cannot be effectively corrected. There is only a small difference in the concentration of carbon dioxide in the blood between causing central sleep apnea and causing arousal. Thus while the physiological principle of using CO2 as a therapy for CSA associated with heart failure is accepted, it has not passed into clinical use principally because of difficulties in titrating and remaining the concentration of inspired CO2 in real time. On the other hand, the current technology is based on an airflow sensor placed at the nasal outlet and two thoracoabdominal bands respectively tied at the chest and abdomen to determine whether the patient is in apnea. The airflow sensor and the thoracoabdominal band may cause discomfort, affecting the patient's sleep and there is no currently available integrative device that can use these data to titrate inspired $CO_2$. Therefore, there is an unmet need for an effective and comfortable carbon dioxide inhalation treatment device for the patients with central sleep apnea, particularly for the patients with heart failure associated with central sleep apnea.

SUMMARY OF THE INVENTION

For overcoming the above defects of the prior technique, a purpose of the present invention is to provide a carbon dioxide inhalation treatment device for central sleep apnea. This device can provide the patients with stable, moderate carbon dioxide, so as to effectively correct the patients' sleep apnea without causing an increase in arousal and microarousal.

In order to achieve the above purpose, the present invention adopts the following technical solution: a carbon dioxide inhalation treatment device for central sleep apnea is provided, which comprises a blower, a gas cylinder filled with carbon dioxide, a mixing chamber, a mask, and a detection mechanism for detecting central apnea; the mask connected via the mixing chamber with the blower through a second pipe, and the gas cylinder is connected to the second pipe through a third pipe; the third pipe is provided with a flow meter. In one embodiment, the device is initially adjusted during an attended study, commonly in a hospital. For this purpose, the therapeutic device will also be used with the detection mechanism comprising at least one pair of electroencephalographic (EEG) recording electrodes for collecting EEG signals, at least one pair of electromyographic (EMG) recording electrodes for collecting diaphragm EMG signals (either from the skin surface or the esophagus), a signal analyzer with amplification, both the EEG recording electrode and the EMG recording electrode being connected to the signal analyzer. This titration system forms part of the Invention.

Preferably, the outer edge of the mask is loosely connected to a face of a patient, for example, a patient afflicted with sleep apnea.

Preferably, the volume percentage of carbon dioxide in the gas cylinder is 5% to 80%. The gas cylinder of the present invention stores high-pressure high-concentration carbon dioxide, such that it can provide the patient with an appropriate concentration of carbon dioxide alter the carbon dioxide is mixed with the air supplied by the blower. In one embodiment, the volume percentage of carbon dioxide in the gas cylinder is further preferably 60% to 80%.

Preferably, there are a plurality of holes disposed along a portion of the mask, which may be evenly divided into two groups that are respectively located on the left and right sides of the mask.

Preferably, the carbon dioxide inhalation treatment device for central sleep apnea also includes an alarm, which is connected with the tubing immediately before its entry to the mask.

This carbon dioxide inhalation treatment device for central sleep apnea works as follows: it is envisaged that the setup and titration will be done in hospital but that the patient will then be discharged with a device which cannot be adjusted by the user and which delivers a prescribed concentration of inspired/Inhaled $CO_2$.

Detail of apparatus for the titration phase is as follows. First the EEG recording electrode is connected to the head of the patient, then placement of an EMG recording electrode on the surface of the chest or in the esophagus for recording of the diaphragm EMG, placing a mask to the patient, starting the blower, and making the blower send a constant flow of air to the mask. In hospital real-time monitoring of the patient's sleep quality, i.e., observing signals displayed on monitor from the EEG recording electrode in conjunction with an the EMG recording electrode, are used by a healthcare personnel to determine the level of inspired/inhaled CO2 required to overcome central sleep apnea.

When the patient experiences an apnea during sleep, healthcare personnel opens the valve of the gas cylinder to permit egress of the carbon dioxide/oxygen mixture, which is subsequently mixed with the constant airflow inputted by the blower and then enters the mask, so as to make the patient inhale an accurately determined and moderate concentration of carbon dioxide to stimulate the respiratory center and correct apnea. In this way the patient's central sleep apnea events is eliminated by gradually increasing the flow of carbon dioxide from the gas cylinder by gradually adjusting the valve of the gas cylinder, until the minimum effective carbon dioxide concentration for the elimination of the central sleep apnea is achieved.

The present invention has the following beneficial effects compared to the prior technique:

1. This carbon dioxide inhalation treatment device for central sleep apnea is mainly composed of a blower, a gas cylinder filled with carbon dioxide and a mask, so as to provide the patients with stable, moderate carbon dioxide through cooperation of the blower, the gas cylinder, the mask and other components, thus effectively correcting the central sleep apnea.

2. The mask in this carbon dioxide inhalation treatment device for central sleep apnea is provided with a through hole, and does not need to be sealed to the face, thereby eliminating the expiratory resistance, reducing discomfort of the treatment, ensuring comfort while the patient falls asleep, and also reducing the impact of the carbon dioxide in the exhaled breath on the inhaled carbon dioxide.

3. With the first pipe and the second pipe of this carbon dioxide inhalation treatment device for central sleep apnea connected by the airbag, the air blown in by the blower can be mixed evenly with the carbon dioxide flowing out of the gas cylinder to ensure the gas uniformity when the gases are mixed after entering the mask, thus ensuring a good treatment effect.

4. The detection mechanism used in the attended titration phase of this carbon dioxide inhalation treatment device for central sleep apnea is mainly composed of an EEG recording electrode, an EMG recording electrode, a signal analyzer with amplification, and replaces the traditional airflow sensor and thoracoabdominal band, thus ensuring the accuracy of the test results and also improving the patients comfort.

In another embodiment, the concentration of inhalable $CO_2$ is sensed by a sensor from a delivery line and adjusted during the titration phase using a regulator placed at the gas cylinder of the device, using information from the EEG and EMG measurements comprising the chest wall or esophageal electromyographic sensors measuring the activity of the diaphragm during sleep.

It is intended that the optimal concentration of inspired $CO_2$ be determined during an attended (and probably in hospital) study using information obtained by diaphragm electromyography (using surface or esophageal electrodes) and the electroencephalograph (EEG) for judgment of sleep; thus the equipment used for the titration phase form part of the invention. The patient is then discharged to use at home the device adjusted to a fixed personally determined concentration of Inspired $CO_2$.

The present invention envisages that the device could be further adapted in the future to include a non-invasive EMG monitor to titrate CO2 delivery more precisely to respiratory activity.

DETAILED DESCRIPTION OF THE INVENTION

To facilitate those skilled in the art to understand the present invention, the present invention will be further described in detail below with reference to drawings and examples.

Example 1

Figure 1:
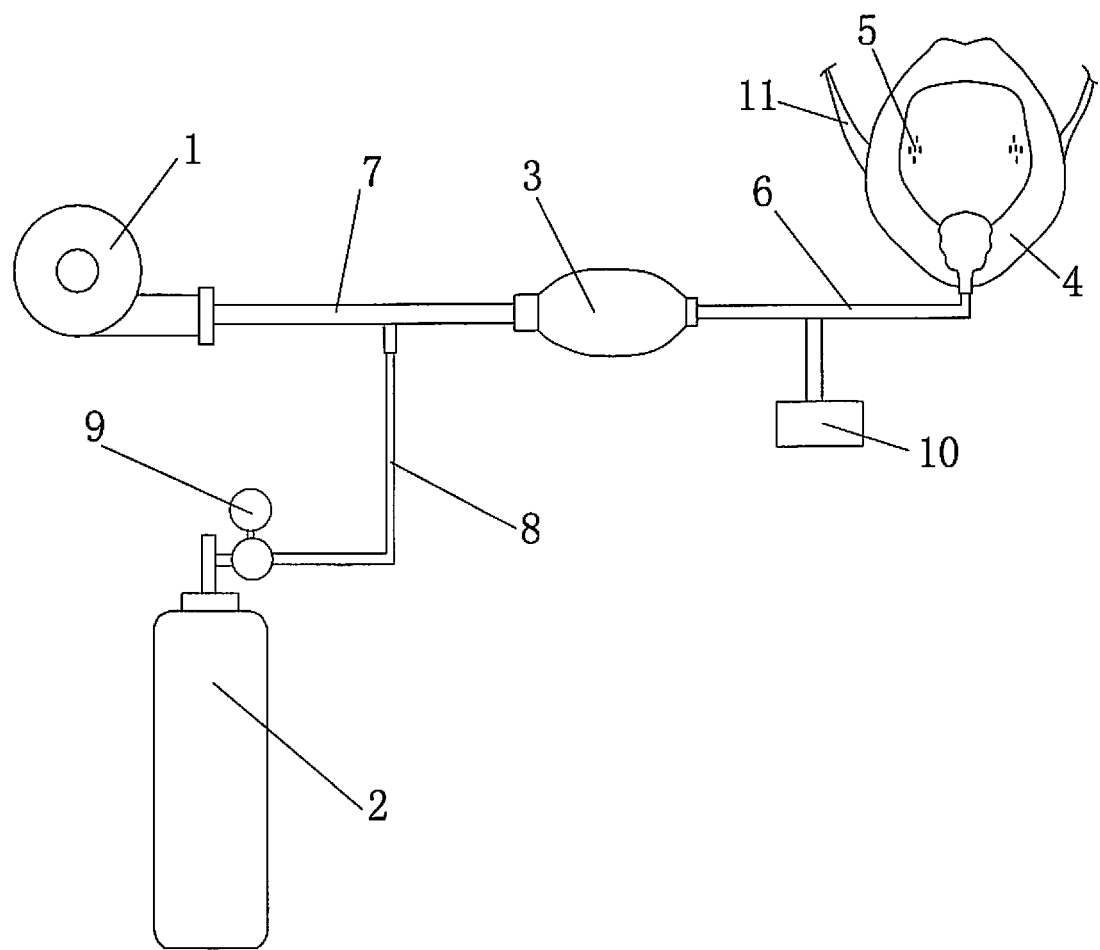
FIG. 1 is a schematic view of the overall structure of a carbon dioxide inhalation treatment device for central sleep apnea according to one embodiment of the Invention.
Figure 2:
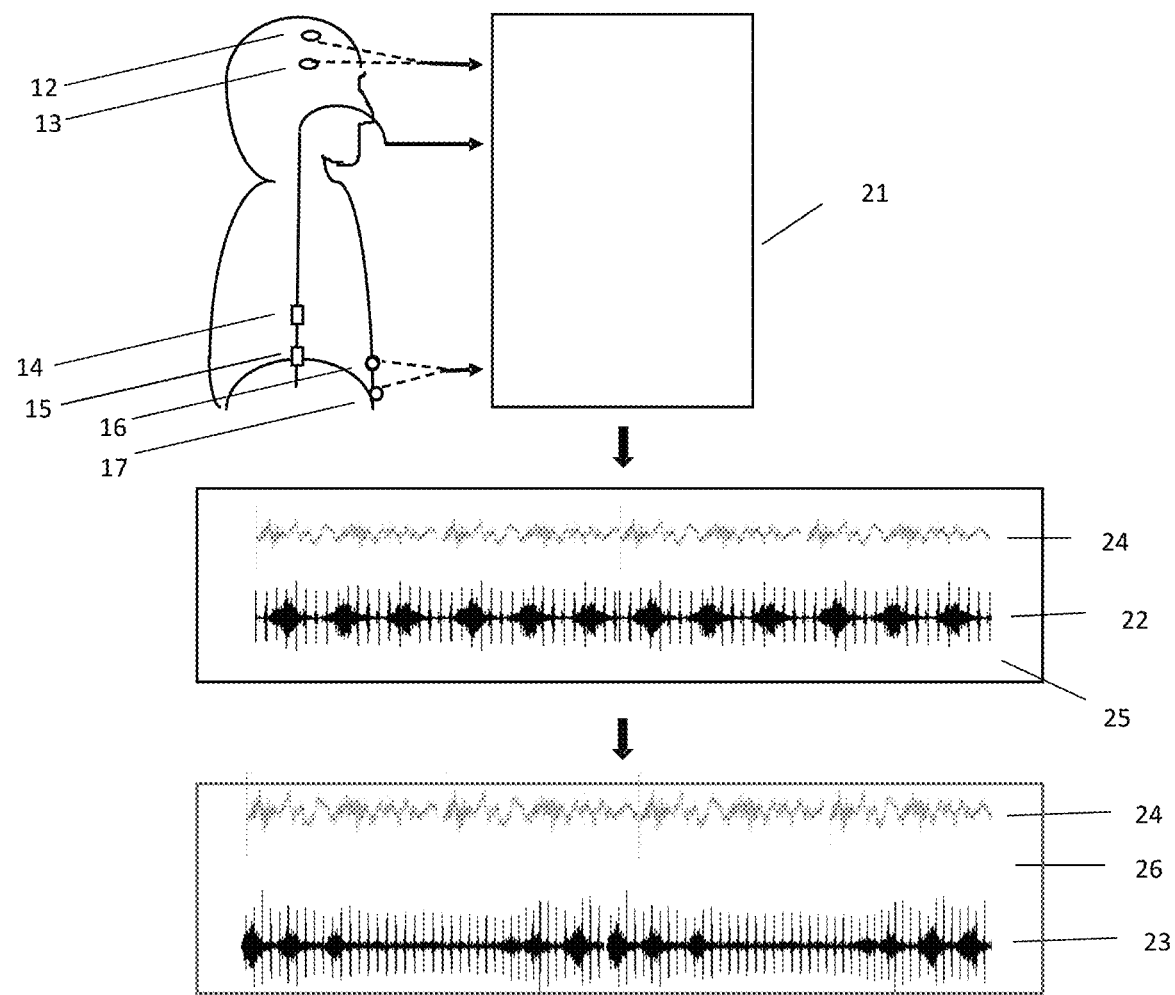
FIG. 2 is a schematic view of the overall system according to one embodiment of the invention, the system comprising a $CO_2$ inhalation device, a detection mechanism, and a signal analyzer.

As shown in FIG. 1, this carbon dioxide inhalation treatment device for central sleep apnea comprises a blower 1, a gas cylinder 2 filled with carbon dioxide, an airbag 3, a mask 4, and a detection mechanism in FIG. 2 for detecting central apnea; the mask 4 is provided with a plurality of holes 5 communicating with the Inside and outside of the mask 4; the mask 4 extends and connects through a first pipe 6 and one end of the airbag 3; the other opposite end of the airbag 3 is connected with the blower 1 via a second pipe 7, and the gas cylinder 2 is connected to the second pipe 7 through a third pipe 8; and the third pipe 8 is provided with a flow meter 9. Specifically, moderate carbon dioxide is supplied stably by the blower 1 and the gas cylinder 2 (i.e., making the patient inhale carbon dioxide at the lowest effective concentration to eliminate central sleep apnea) to stimulate the respiratory center, thus effectively correcting the central sleep apnea, with the patient not be awakened caused by too high concentration of carbon dioxide, thereby improving the sleep quality of the patient. The gases stored in the gas cylinder 2 also include oxygen in addition to carbon dioxide, in which the volume percentage of carbon dioxide is up to 80%, and the volume percentage of oxygen is at least 20%.

FIG. 2, shows a schematic of the overall system, comprising the detection mechanism used in the attended titration phase comprising at least one pair of EEG recording electrodes consisting of electrodes 12 and 13 for collecting EEG signals 24, at least one pair of EMG recording electrodes consisting of electrodes 14 and 15 for esophageal recording or electrodes 16 and 17 for chest wall recording to collect diaphragm EMG signals 22 and 23. Both the EEG recording electrode 12 and 13 and the EMG recording electrode 14 and 15 for esophageal recording or electrodes 16 and 17 for surface recording being displayed on monitor 25 or 26. In this example, one pairs of the EEG recording electrodes 12 and 13 are used that are attached to a patient's head, so as to monitor the patient's sleep status in real time. The EMG recording electrode may be a recording electrode disposed in the esophagus, or placed on both sides of the chest. In this example, the EMG recording electrode 16 and 17 is paced on chest wall to monitor or detect the central apnea by the presence or absence of myoelectricity. On monitor screen 25, EMG 22 exists during sleep as judged by EEG signal 24, indicating no sleep apnea. On monitor screen 26, EMG 23 disappear over a period time during sleep as judged by EEG signal 24, indicating there were central sleep apnea events.

The outer edge of the mask 4 is loosely connected to the face of a patient. Loose connection means that the mask 4 and the face can be spaced rather than be connected in a sealed manner, which allows leakage, thus ensuring comfort of the patient wearing the mask.

In another embodiment, the carbon dioxide inhalation treatment device for central sleep apnea also includes an alarm 10, which is connected with the first pipe 6. The alarm 10 may monitor the concentration of carbon dioxide through the first pipe 6 at any time; when the concentration of carbon dioxide is high, the alarm 10 issues an alarm signal to prevent the patient from inhaling excessive carbon dioxide due to device failure, thus ensuring the patient's safety.

There are a plurality of holes 5, which are evenly divided into two groups that are respectively located on the left and right sides of the mask 4. This arrangement assures the smoothness of the exhaust of the mask 4, and Improves the comfort.

The use process of the carbon dioxide inhalation treatment device for central sleep apnea is described as follows:

Affixing the EEG recording electrodes 12 and 13 to the head of the patient, then placing the EMG recording surface electrodes 16 and 17 on the chest of the patient, aligning the mask 4 to the patient along the face, covering the nose and mouth, and securing the mask in position using a strap or rope 11, and then starting the blower 1, and making the blower 1 send a constant flow of air to the mask 4. Real-time monitoring the patient's sleep breathing condition, i.e., the signals detected by the EEG electrode and the EMG electrodes are displayed on the monitor as shown on monitor screen 25 or 26 after signal analyzer 21, with the patient assessed for central sleep apnea based on the signal displayed on the monitor.

When the patient falls asleep after the intermittent disappearance of the respiratory muscle myoelectricity as shown on monitor 26, gradually opening the valve of the gas cylinder 2 by starting from the flow rate of 0.1 i/min displayed on the flow meter 9 according to the intermittent disappearance of the respiratory muscle EMG. With the respiratory muscle EMG disappearance occurring two times within 10 min, increasing the flow rate of carbon dioxide of the gas cylinder to 0.05 L/min and gradually increasing concentration of the inhaled carbon dioxide, until the respiratory muscle EMG has no more intermittent disappearance as shown on monitor screen 25. When the lowest effective carbon dioxide concentration is achieved, fixing the valve to let the subject continue to be treated.

Example 2

This carbon dioxide inhalation treatment device for central sleep apnea is the same as Example 1 except for the following technical feature: The volume percentage of carbon dioxide in the gas cylinder is 60%.

Example 3

This carbon dioxide inhalation treatment device for central sleep apnea is the same as Example 1 except for the following technical feature: The volume percentage of carbon dioxide in the gas cylinder is 80%.

Example 4

This carbon dioxide inhalation treatment device for central sleep apnea is the same as Example 1 except for the following technical feature: The volume percentage of carbon dioxide in the gas cylinder is 5%.

The above-described embodiments are preferred examples of the present invention; however, the present invention is not limited thereto, and other variations that do not depart from the technical solution of the present invention or other equivalent permutations are included within the scope of protection of the present invention.

What is claimed is:

1. A carbon dioxide inhalation treatment device for central sleep apnea, comprising:
 a blower,
 a gas cylinder filled with a minimum volume percentage of 20% oxygen and 5%—80% of carbon ioxide ($CO_2$),
 a mixing chamber, connected to the blower and the gas cylinder, wherein inhalable $CO_2$ from the gas cylinder is configured to be driven by air using the blower,
 a mask configured to be worn by a user for receiving the inhalable $CO_2$, wherein multiple holes are disposed along a portion of the mask, the holes providing a communication between an inside and outside of the mask, and an outer edge of the mask is configured to be loosely connected to a face of the user and
 a detection mechanism for detecting central apnea configured to measure the presence or absence of myoelectricity as measured by an EMG signal or both of an EEG signal and an EMG signal.

2. The device of claim 1, wherein the mask is connected to the mixing chamber at an end via a first conduit comprising a pipe or tube, and wherein the blower and gas cylinder are connected to an opposite end of the mixing chamber via an interconnected conduit comprising a second conduit comprising a second pipe or tube and a third conduit comprising a third pipe or tube.

3. The device of claim 1, wherein the plurality of holes are evenly divided into two groups that are respectively located on left and right sides of the mask.

4. The device of claim 1, characterized in that: the volume percentage of carbon dioxide in the gas cylinder is 20% to 80%.

5. The device of claim 1, further comprising an alarm alert connected with the first conduit configured to monitor the concentration of carbon dioxide.

6. The device according to claim 1, wherein the detection mechanism is configured to adjust the concentration of inhalable carbon dioxide administered by the treatment device, until an EMG signal no longer presents an intermittent disappearance indicating a sleep apnea event; the carbon dioxide treatment device configured to maintain an optimal concentration of carbon dioxide, via the detection mechanism, for administration to the user by inhalation via the mask of the treatment device.

7. The device of claim 6, further comprising a titration mechanism comprising at least one pair of electroencephalographic recording electrodes worn by the user for collecting EEG signals, at least one pair of surface or esophageal electromyographic recording electrodes worn by the user for collecting diaphragm EMG signals, a signal amplifier and a signal analyzer, the recording electrodes being connected to the signal analyzer through the signal amplifier.

8. A method of treating central sleep apnea, comprising: administering an inhalable $CO_2$ treatment concentration to a patient via a carbon dioxide inhalation treatment device according to claim 1.

9. The method according to claim 8, wherein the inhalable $CO_2$ treatment concentration is determined by using a titration mechanism for measuring the presence or absence of myoelectricity as measured by an EMG signal or both of an EEG signal and an EMG signal of the patient, and adjusting the concentration of inhalable carbon dioxide administered by the treatment device, until the patient's EMG signal no longer presents an intermittent disappearance indicating a sleep apnea event.

10. The method according to claim 9, whereby the concentration of inhalable $CO_2$ is sensed by a sensor from a delivery line and adjusted during a titration phase using a regulator placed at the gas cylinder of the device, using information from chest wall or esophageal electromyographic sensors measuring activity of a diaphragm of the patient during sleep.

11. The method according to claim 8, further comprising maintaining an optimal concentration of carbon dioxide, via a detection mechanism, and administering a fixed and non-adjustable amount of carbon dioxide to the patient by inhalation via the mask of the treatment device.

* * * * *